US008338333B1

(12) United States Patent
Molin et al.

(10) Patent No.: US 8,338,333 B1
(45) Date of Patent: Dec. 25, 2012

(54) METHODS FOR CONTROLLING WEEDS INCLUDING KUDZU

(75) Inventors: William T. Molin, Greenville, MS (US); Margaret E. Lyn, Atlanta, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 59 days.

(21) Appl. No.: 12/953,705

(22) Filed: Nov. 24, 2010

Related U.S. Application Data

(60) Provisional application No. 61/264,343, filed on Nov. 25, 2009.

(51) Int. Cl.
*A01N 57/00* (2006.01)
(52) U.S. Cl. ...................................... 504/128
(58) Field of Classification Search ........................ None
See application file for complete search history.

(56) References Cited

U.S. PATENT DOCUMENTS

| | | | | |
|---|---|---|---|---|
| 6,165,939 A | * | 12/2000 | Agbaje et al. | 504/105 |
| 2006/0063678 A1 | * | 3/2006 | Wright et al. | 504/206 |
| 2010/0331185 A1 | * | 12/2010 | Abribat et al. | 504/206 |
| 2011/0105328 A1 | * | 5/2011 | Chavant et al. | 504/128 |

OTHER PUBLICATIONS

State Noxious Weed Control Board, Kudzu (*Pueraria lobata*), www.nwcba.wa.gov/weed_info/Pueraria_lobata.html, 2003.
Berisford, Y.C. et al., Leaching and Persistence of Herbicides for Kudzu (*Pueraria montana*) control on Pine Regeneration Sites, Weed Science, 2006, 54: 391-400.
Ezell, A.W. et al.; Comparison of Treatments of Controlling Kudzu Prior to Planting Tree Seedlings, Citation for proceedings: Connor, Kristina F., ed. 2006/ Proceedings of the 13th biennial southern silvicultural research conference. Gen. Tech. Rep. SRS-92. Asheville, NC: U.S. Department of Agriculture, Forest Service, Southern Research Station, pp. 148-149.
Forseth, I.N. et al., Kudzu (*Pueraria montana*): History, Physiology, and Ecology Combine to Make a Major Ecosystem Threat, Critical Reviews in Plant Sciences, 2004, 23(5): 401-413.
Miller, J.H., Kudzu Eradication Trials with New Herbicides, In: Proceedings, 41st Annual Meeting Souther Weed Science Society; 1988, 220-225.
Mitchell, G. et al., Mesotrione: A New Selective Herbicide for Use in Maze, Pest Management Science, 2001, 57: 120-128.
Nelson, L.R., Kudzu Eradication Guidelines, 2003, www.clemson.edu/extfor/publications/ec656.

* cited by examiner

*Primary Examiner* — Alton Pryor
(74) *Attorney, Agent, or Firm* — John D. Fado; G. Byron Stover

(57) ABSTRACT

A method for killing weeds (e.g., kudzu) involving applying to weeds a herbicidally effective amount of a herbicidal composition comprising glyphosate and at least one acetolactate synthase inhibitor (e.g., trifluxosulfuron, pyrithiobac, flumetsulam).

4 Claims, 4 Drawing Sheets
(4 of 4 Drawing Sheet(s) Filed in Color)

METHODS FOR CONTROLLING WEEDS INCLUDING KUDZU

REFERENCE TO RELATED APPLICATION

This application claims the benefit of U.S. Provisional Application No. 61/264,343, filed 25 Nov. 2009, which is incorporated herein by reference in its entirety.

BACKGROUND OF THE INVENTION

The present invention relates to a method for killing weeds (e.g., kudzu) involving applying to weeds a herbicidally effective amount of a herbicidal composition comprising glyphosate and at least one acetolactate synthase inhibitor (e.g., trifluxosulfuron, pyrithiobac, flumetsulam).

Kudzu, *Pueraria montana* (Lour.) Merr. variety *lobata* (Willd.), is a perennial, deciduous, semi-woody vine with a well developed root system (Forseth, I. N., Jr., and A. F. Innis, Critical Reviews in Plant Sciences, 23: 401-413 (2004)). Originating from China and native to Japan, kudzu was introduced to the United States in 1876 at the Centennial Exposition in Philadelphia. During the Great Depression, kudzu was promoted as a means of erosion control. The so-called "miracle vine" grew and spread too fast because it was imported without its natural predators. In 1972, the Department of Agriculture officially declared kudzu a weed. Under ideal weather conditions, a temperate, moderately wet climate, as typically found in the southeastern United States, kudzu overtakes most everything in its path, in the process harming forests by shielding light from trees and distorting the landscape with its accumulated weight. For Southern farmers, landscapers and citizens, it is a major problem. Now infesting over 7 million acres of the southeastern United States, and spreading at a rate of 120,000 acres per year, this plant represents a serious threat to productivity in its growing region.

Each year, a new network of stems and branches develop from overwintering crowns of kudzu tap roots. Crowns may produce up to 30 vines with multiple branches (Anonymous, 2003, Kudzu (*Pueraria lobata*), http://www.nwcb.wa.gov/weed_info/-Pueraria_lobata.html). Kudzu stems and leaves continuously overgrow each other, forming dense, multi-layered mats that may be more than a meter thick. Nodes and internodes of vines that come in contact with soil may root and form new crowns. Connections between crowns may disintegrate leaving independent ramets (Forseth and Innis 2004), each capable of developing multiple branches. Kudzu vines may grow up to 18 m/yr (Michael, J. L., Pine regeneration with simultaneous control of kudzu, In: Proceedings, 35th Annual Meeting, Southern Weed Science Society, 1982, Atlanta, Ga., pages 282-288) and quickly cover large areas. These morphological traits make mature stands of kudzu one of the most difficult weeds to control (Nelson, L. R., 2003, Kudzu eradication guidelines, http://www.clemson.edu/extfor/-publications/ec656/).

Kudzu eradication is dependent upon killing all crowns because a few surviving crowns can quickly lead to re-establishment. However, injured crowns may not sprout for two years, thus necessitating eradication efforts over several years (Nelson 2003). Any portion of the root system surviving herbicide treatment may produce new growth (Edwards, M. B., Kudzu-ecological friend or foe, In: Proceedings, 35th Annual Meeting, Southern Weed Science Society, 1982, Atlanta, Ga., pages 232-236).

Herbicide programs have mainly focused on mature, actively growing stands of kudzu. In mature stands, it is difficult to achieve adequate herbicide coverage with all living tissues because of dense layers of foliage. For example, in one study thirteen applications of 2,4,5-trichlorophenoxyacetic acid over a five year period was not successful in killing all crowns (Davis, D. E., and H. H. Funderburk, Weeds, 12: 63-65 (1963)). Some herbicides recommended for control of kudzu are unattractive because they have high soil persistence or are highly leachable thus threatening groundwater safety (Berisford, Y. C., et al., Weed Science, 54: 391-400 (2006); Harrington, T. B., et al., Weed Science, 51: 965-974 (2003)).

Thus there is a need for an effective herbicide to control weeds such as kudzu.

SUMMARY OF THE INVENTION

In accordance with the present invention there is provided a method for killing weeds (e.g., kudzu) involving applying to weeds a herbicidally effective amount of a herbicidal composition comprising glyphosate and at least one acetolactate synthase inhibitor showing activity against kudzu (e.g., trifluxosulfuron, pyrithiobac, flumetsulam).

BRIEF DESCRIPTION OF THE DRAWINGS

The patent or application file contains at least one drawing executed in color. Copies of this patent or patent application publication color drawing(s) will be provided by the Office upon request and payment of the necessary fees.

DETAILED DESCRIPTION OF THE INVENTION

Figure 1:
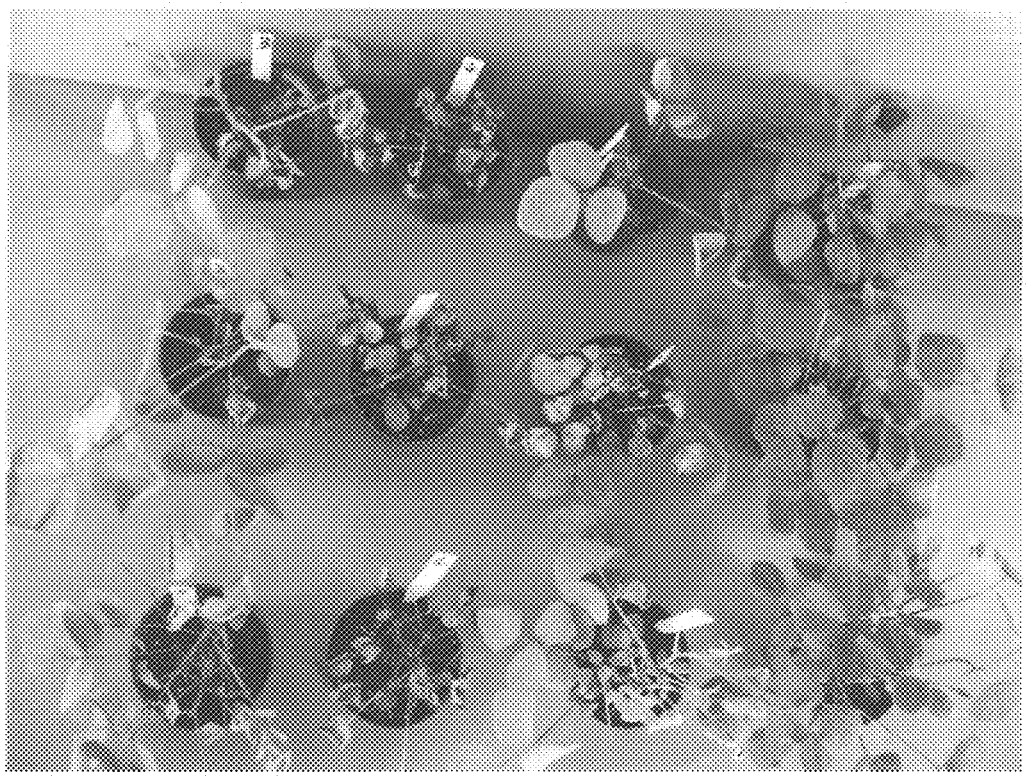
FIG. 1 shows effects of glyphosate, glyphosate trifloxysulfuron mixture, and trifloxysulfuron compared to untreated plants of kudzu at one week after treatment as described below. Control plants on right.

Presently, relatively few herbicides are labeled for kudzu control and many are restricted use products. Our invention enables reclamation of kudzu infested land for agronomic use and improves kudzu control with lower than generally recommended glyphosate rates and fewer applications in a shorter timeframe, and provides greater and longer lasting levels of control because it delays or prevents regrowth of vines. Present control measures generally require expensive and time consuming manual and chemical strategies, estimated at $200 to $2,000 per acre, that are often repeated at high rates over several years. Currently it is recommended that repeated applications of glyphosate (as WeatherMax™) alone be used at 80 to 106 fl oz per acre for kudzu control. Our invention surprisingly reduces this rate to about 22 fl oz per acre when used in combination with an acetolactate synthase (ALS) inhibitor. Our invention can be used by anyone wanting to remove kudzu from infested lands such as fields, pastures, orchards, forests, and the adjoining roadsides, ditch banks, power and phone lines, and rights-of-way. Users may include personnel in parks and recreation departments, state and local transportation departments, and power and other utility companies.

We found that a combination of glyphosate plus certain acetolactate synthase (ALS) inhibitors, such as trifloxysulfuron (pyrithiobac, metsulfuron methyl), surprisingly caused rapid necrosis of treated kudzu tissues at rates faster than what would be expected by those skilled in weed control. Without being bound by theory, this combination produces an additive or synergistic effect resulting in rapid deterioration of treated tissues compared to tissues to which these herbicides were applied alone. As both herbicides are slow acting, the early appearance of injury was a surprise. Furthermore, the enhanced effect by the combination can occur at a reduced rate (up to 63% less) for one of the herbicides (e.g., glyphosate) which means there is less chance of damaging sensitive neighboring plants. In greenhouse trials, glyphosate plus trifloxysulfuron provided significant control of kudzu (>95%) compared to several other mixtures at reduced rates. In field trials, glyphosate plus trifloxysulfuron greatly reduced kudzu regrowth compared to other mixtures. These results demonstrate that these mixtures are surprisingly useful in stemming the spread of weeds such as kudzu.

Compounds that inhibit the catalytic action of acetolactate synthase are collectively called acetolactate synthase (ALS) inhibitors. The ALS inhibitor family includes (1) sulfonylureas such as chlorosulfron and thifensulfuron methyl, (2) imidazolinones such as imazapyr and imazaquin, (3) triazolopyrimidine sulfonanilides such as flumetsulam, and (4) pyrimidinylsalicylic acids such as pyrithiobac sodium and carbonyl-triazolines (Plant amino acids: biochemistry and biotechnology (1998) by Bijay Singh).

Generally, the herbicide mixtures (i.e., glyphosate plus an acetolactate synthase (ALS) inhibitor) can be applied throughout the growing season. Early application in Spring to actively growing vines (i.e., younger vines or tissues) is preferred. Also preferred is Autumn application, especially before an anticipated frost, which allows uptake and translocation of the herbicides. Autumn applications also allows sufficient time for translocation to the root system.

Generally, on mature vines, rates from about 1 to about 2 lb per acre (e.g., 1-2 lb per acre) of glyphosate, plus about 0.15 to about 0.30 oz. per acre (e.g., 0.15 to 0.30 oz. per acre) trifluxosulfuron, or about 1.8 to about 3.6 oz. per acre (e.g., 1.8 to 3.6 oz. per acre) pyrithiobac, or about 1.3 to about 2.6 oz per acre (e.g., 1.3 to 2.6 oz per acre) flumetsulam can be used. Multiple applications can be made if regrowth occurs, and as frequently as necessary to suppress kudzu populations below tolerance levels. However, because regrowth is suppressed by these herbicidal mixtures, repeat applications at lower use rates may be preferred instead of higher rates.

The present invention is directed to a method of killing or controlling weeds or unwanted plants. The method comprises applying a herbicidally effective amount of glyphosate plus an acetolactate synthase (ALS) inhibitor to foliage of the weeds or unwanted plants (e.g., poison ivy, poison oak, kudzu, multiflora rose, golden rod, blue fescue, red maple, and/or red oak). The herbicidal compositions may be used to control a very wide variety of plant species worldwide. Particularly important genera for which the herbicidal compositions are used are exemplified without limitation by the following:

Annuals, including Barnyard grass (*Echinochloa crusgalli*); Beggarweed, Florida (*Desmodium tortuosum*); Bristly starbur (*Achillea millefolium*); Broadleaf signalgrass (*Brachiaria platyphylla*); Carpetweed (*Mollugo verticilata*); Chickweed (*Stellaria media*); Cocklebur, common (*Xanthium* spp.); Corn, Volunteer (non-it/ir) (*Zea mays*); Hemp sesbania (*Sesbania exaltata*); Henbit (*Lamium amplexicaule*); Jimsonweed (*Datura stramonium*); Kochia (*Kochia scoparia*); Lambsquarters, common (*Chenopodium album*); Morningglory, entireleaf (*Ipomoea* spp.); Morningglory, ivyleaf; Morningglory, pitted; Morningglory, tall; Mustard, wild (*Brassica* spp.); Nightshade species (*Solanum* spp.); Pigweed, Palmer (*Amaranthus* spp.); Pigweed, redroot; Pigweed, smooth; Pigweed, tall waterhemp; Purslane, common (*Portulaca* spp.); Ragweed, common (*Ambrosia* spp.); Ragweed, giant; Shepherd's purse (*Capsella bursa-pastoris*); Sicklepod (*Cassia oblusifolia*); Smartweed, Pennsylvania (*Polygonum* spp.); Spurge, nodding (*Euphorbia* spp.); Spurge, spotted; Sunflower, common (*Helianthus* spp.); Velvetleaf (*Abutilon theophrasti*).

Perennials, including Bermudagrass (*Cynodon dactylon*); Kudzu (*Pueraria* spp.); Johnsongrass (seedling) (*Sorghum halepense*); Marestail/horseweed (*Conyza canadensis*); Nutsedge, yellow (*Cyperus esculentus*); Nutsedge, purple (*C. rotundus*). Also Redvine (*Brunnichia ovata*).

The method of the present invention may be useful on any of the above species.

Unless defined otherwise, all technical and scientific terms used herein have the same meaning as commonly understood by one of ordinary skill in the art to which the invention belongs. The term "about" is defined as plus or minus ten percent; for example, about 100° F. means 90° F. to 110° F. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Greenhouse trials: Kudzu was established from seed in flats containing a 2:3 (w:w) mixture of soil (Bosket silt clay loam, fine-silty, mixed thermic Aeric Ochraqualf) and potting media. Seedlings were transferred to 10 cm diameter pots containing the same soil mixture when they developed two true leaves. Pots were placed in the greenhouse, set at 30°±2° C., and equipped with supplemental lighting to provide a 14-h photoperiod. Pots were irrigated as needed and fertilized every three weeks with slow release Osmocote® fertilizer at 1.5 g/pot. Herbicides were applied when the main axis of the plants had 7 to 8 nodes and had a length of 45 cm. Plants were selected for size uniformity from a population of approximately three times that necessary to establish a test.

Herbicides were applied with a pneumatic track sprayer with a TeeJet 8002 flat-fan nozzle delivering 187 L/ha water at 179 kPa. The rates utilized in this study were based on the allowable rates according to the label of the herbicide containers. The rates for the herbicides are listed in the tables below. Kudzu was evaluated for herbicide injury expressed as the percentage of above-ground green biomass remaining at 2 weeks after treatment (WAT) compared to untreated plants (control) on a dry weight basis. Treatments were arranged in a randomized complete block design with four replications and the experiment was repeated. Data were analyzed using the Proc Mixed procedure in SAS and means were separated using a Fisher's Protected least significant difference (LSD) at P=0.05.

Field trials: Uniform areas of land infested with kudzu were identified in Holcomb and Yazoo City, Miss. Plots were one by two meters separated by a narrow strip to prevent cross-contamination of herbicides in Holcomb. Plots were three by three meters in Yazoo City. Herbicides were applied with an hand held boom sprayer equipped with a Teejet 8002

EVS flat fan nozzles, adjusted to 207 kPa, and applied at 1.3 m/s in a single pass to deliver 61.2 L/ha to the treatment areas. Commercial formulations of herbicides were applied at their maximum labeled rates. Herbicides were applied to both sites in mid September. In Holcomb, vegetation within a 0.3 m$^2$ area of each test plot was harvested at 6 weeks after treatment. Green plant matter was collected and dried as an estimate of above-ground healthy biomass. Biomass of treated plots was compared to untreated plots to determine percent control. In Yazoo City, the percentage reduction in leaf cover was determined by counting the number of leaves intersected by a grid containing 100 intersections (at 10 centimeter intervals) per one meter square.

Example 1

In greenhouse studies, shoot biomass was determined at 2 WAT. Most treatments surprisingly provided better than 90% control (Table 1). In particular, combinations of glyphosate plus an acetolactate synthase (ALS) inhibitor, such as trifloxysulfuron, surprisingly caused rapid necrosis of treated tissues and prevented resprouting of vines (Table 1). This observation was unexpected and important because of the surprisingly rapid desiccation and biomass reductions (FIG. 1); note the rapid burn down effect on plants in the second column following glyphosate trifloxysulfuron treatment. For those skilled in the art of weed control, enhanced control resulting from glyphosate and an ALS inhibitor would not be expected. It is important to note that not all acetolactate inhibitors caused inhibition of kudzu growth. Those with high initial activity against kudzu may provide suitable kudzu control when mixed with glyphosate.

Example 2

Increasing the number of combinations and rates for trifloxysulfuron and glyphosate surprisingly showed that reduced rates were also effective (Table 2). The labeled recommended rate of glyphosate for kudzu control was 80 to 106 ounces per acre which was well above the rates tested herein. In Table 2 the rates were 8, 16 and 22 oz formulated glyphosate (WeatherMax™) per acre with trifloxysulfuron at 4.25 grams per acre. The ability to achieve control of kudzu at reduced rates of herbicide was a further indication that a unique effect was observed and allowed control using less pesticide.

Example 3

Although the combination of atrazine or metribuzin plus glyphosate provided excellent initial control of kudzu in the greenhouse, in field trials these combinations were inferior in comparison to the glyphosate-ALS inhibitor combination in suppressing regrowth (Table 3). Translocation of herbicides to roots is vital to achieving control of established perennial species like kudzu having deep root systems and a high capacity for regrowth. Other weeds such as redvine, silverleaf nightshade, and yellow and purple nutsedge with deep perenniating underground structures may also be more easily controlled. Without being bound by theory, the field application occurred in September when carbon allocation in kudzu shifts to root reserve replenishment which could facilitate herbicide translocation and may account for the greater activity of the combination of trifloxysulfuron and glyphosate on suppressing regrowth. Hence, timing application in the field may be an important factor in establishing the efficacy of these mixtures.

Example 4

Figure 4:
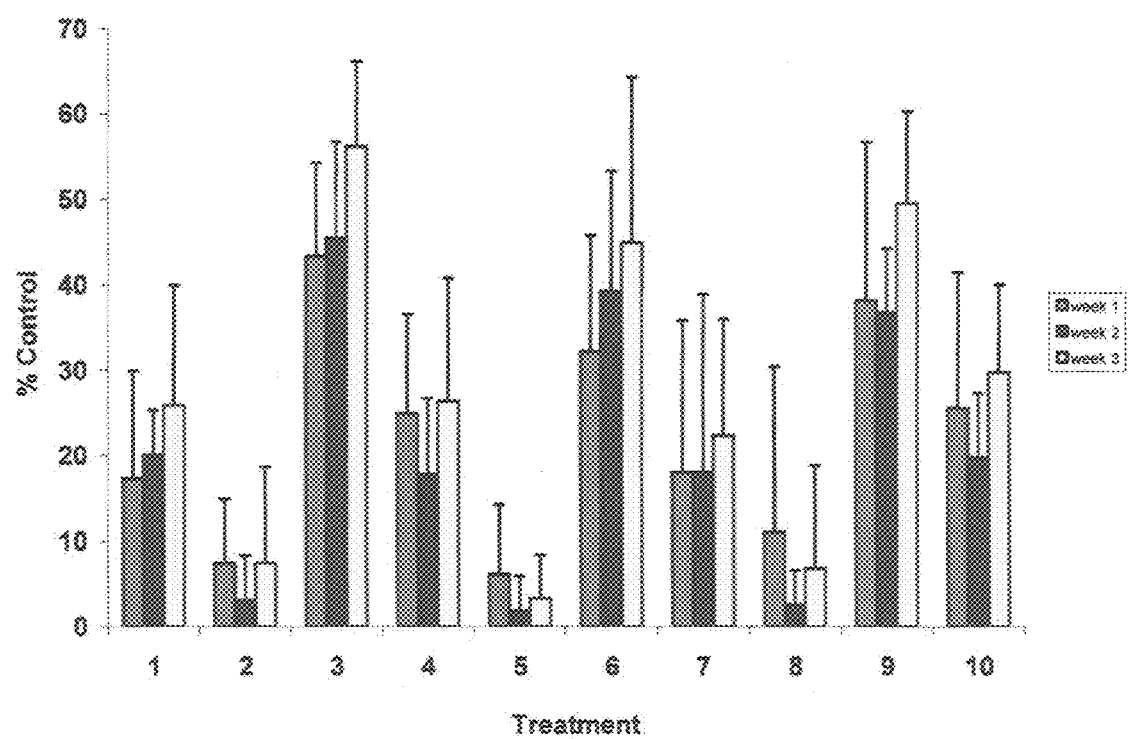
FIG. 4 shows control of mature kudzu vines at 1, 2 and 3 weeks after treatment as described below. Treatment information is summarized in Table 4.

Table 4 provides a list of combination of glyphosate with common ALS inhibitors. The labeled recommended rate of glyphosate, for kudzu control was 80 to 106 ounces per acre which was well above the rates tested herein. ALS inhibitors were used at label rates. Post-emergence applications of the treatments listed in Table 4 were made to mature kudzu stands growing over a Bermuda grass turf. FIG. 4 shows the efficacy of single application of these treatments. When ALS inhibitors were applied alone, less than 10% control was observed 3 WAT, whereas glyphosate alone provided less than 26% control. However, when glyphosate was combined with an ALS inhibitor, the level of control surprisingly increased to 45-56% (FIG. 4).

Example 5

Figure 2A:
FIGS. 2a and 2b show kudzu plots of an untreated control and a plot treated with the glyphosate trifloxysulfuron mixture in the field at four weeks after treatment as described below.
Figure 2B:
Figure 3A:
FIGS. 3a and 3b show the same plots as in FIGS. 2a and 2b at 7 months after treatment as described below.
Figure 3B:
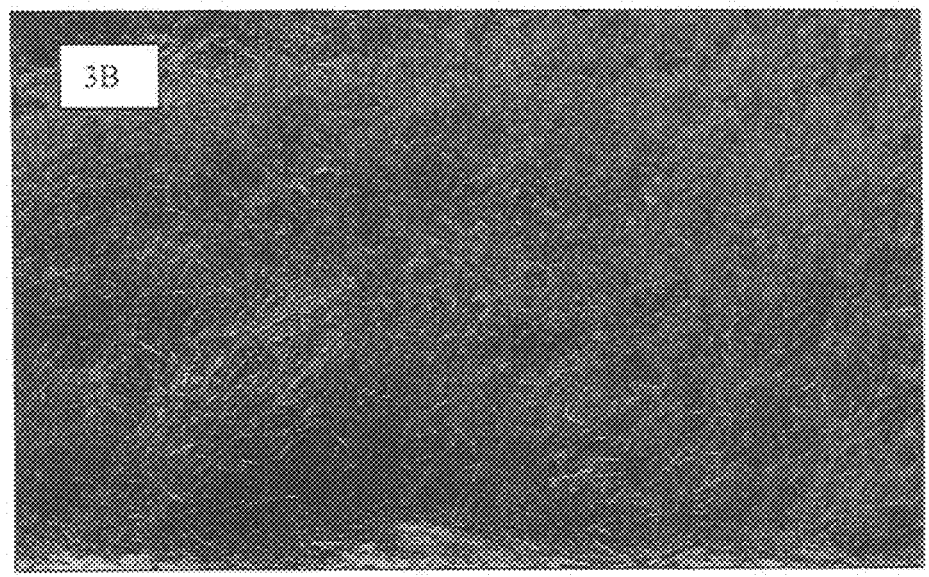

FIG. 2 shows the effect of a glyphosate trifloxysulfuron mixture on kudzu (FIG. 2B) at four weeks after treatment (Oct. 19, 2009) compared to an untreated area (FIG. 2A). The percentage reduction in leaf biomass was surprisingly 83% at four weeks after treatment at the lower treatment rate. Surprisingly, regrowth of kudzu in plots the following spring was greatly reduced (FIG. 3A compared to 3B). These results demonstrated the unique activity of the glyphosate trifloxysulfuron mixture applied to kudzu in the Fall and the resulting sustained control the following Spring. Thus, a single application of the mixture reduced re-growth and re-establishment of kudzu.

The cost to control kudzu with present herbicides labeled for kudzu control such as metsulfuron methyl, picloram, triclopyr and clopyralid are in the range of $50 to $100 per acre. This invention discloses a cost ranges from $17 to $40 per acre. Without being bound by theory, this invention takes advantage of two different modes of action at a reduced cost which should make kudzu control more cost efficient and avoids the use of a restricted use such as picloram; the use of two different modes of action and the reduced rate of glyphosate may reduce the incidence of resistance.

All of the references cited herein, including U.S. Patents, are incorporated by reference in their entirety. Also incorporated by reference in their entirety are the following references:_Berisford, Y. C., et al., Weed Science, 54: 391-400 (2006); Dickens, R., and G. A. Buchanan, Weed Science, 19: 669-671 (1971); Rader, L. T., et al., An integrated pest management research program for kudzu (*Pueraria lobata*) at the Savannah river site, South Carolina, In: Proceedings, 52nd Annual Meeting, Southern Weed Science Society, 1999, Greensboro, N.C., page 404); Smith, A. E., Evaluation of new herbicides for controlling kudzu, In: Proceedings, 41st Annual Meeting, Southern Weed Science Society, 1988, Tulsa, Okla., page 260).

Thus, in view of the above, the present invention concerns (in part) the following:

A method for killing weeds (or inhibiting growth and regrowth), said method comprising (or consisting essentially of or consisting of) applying to said weeds a herbicidally effective amount (or growth and regrowth inhibiting amount) of a herbicidal composition comprising (or consisting essentially of or consisting of) glyphosate and at least one acetolactate synthase inhibitor showing activity against kudzu.

The above method, wherein said weeds are kudzu.

The above method, wherein said herbicidal composition is applied to weeds in Autumn.

The above method, wherein said herbicidal composition is applied to weeds in Spring.

The above method, wherein said at least one acetolactate synthase inhibitor is selected from the group consisting of trifluxosulfuron, pyrithiobac, flumetsulam, and mixtures thereof. The method wherein said method comprises applying about 1 to about 2 lb of glyphosate per acre plus about 0.15 to about 0.30 oz. per acre trifluxosulfuron or about 1.8 to about 3.6 oz. per acre pyrithiobac or about 1.3 to about 2.6 oz per acre flumetsulam. The above method, wherein said at least one acetolactate synthase inhibitor is trifluxosulfuron. The above method, wherein said at least one acetolactate synthase inhibitor is pyrithiobac. The above method, wherein said at least one acetolactate synthase inhibitor is flumetsulam.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Effect of herbicides on kudzu control based on percent reduction of above-ground green biomass.

| Herbicide treatments | Target crop | Rate (units/A) | Control (%) |
|---|---|---|---|
| glyphosate | corn soybean cotton | 1.1 lb | 50 |
| atrazine | corn | 1.6 lb | 93 |
| glyphosate + atrazine | corn | 1.1 lb + 1.6 lb | 95 |
| atrazine + mesotrione | corn | 0.25 lb + 0.25 lb | 99 |
| glyphosate + carfentrazone | corn | 1.1 lb + 29 ml | 97 |
| flumetsulam | corn | 1.3 oz | 99 |
| acifluofen + bentazon | soybean | 0.75 lb | 64 |
| metribuzin | soybean | 1 lb | 98 |
| glyphosate + metribuzin | soybean | 1.1 + 1 lb | 94 |
| pyrithiobac | cotton | 29 g | 78 |
| glyphosate + pyrithiobac | cotton | 1.1 lb + 29 g | 100 |
| prometryn | cotton | 0.5 lb | 96 |
| glyphosate + prometryn | cotton | 1.1 lb + 0.5 | 95 |
| trifloxysulfuron | cotton | 4.25 g | 93 |
| glyphosate + trifloxysulfuron | cotton | 1.1 lb + 4.25 g | 100 |
| prometryn + trifloxysulfuron | cotton | 1 lb + 4.25 g | 99 |
| oxyfluorfen + MSMA | cotton | 1 pt + 2 lb | 57 |
| fluometuron + MSMA | cotton | 1 lb + 2 lb | 77 |
| prometryn + MSMA | cotton | 0.5 lb + 2 lb | 83 |
| metsulfuron | non-crop | 0.06 oz | 87 |
| halosulfuron | corn | 19 g | 3 |
| imazaquin | soybean | 0.125 lb | 3 |
| primisulfuron | corn | 0.044 lb | 1 |
| chlorimuron | soybean | 22 g | 0 |
| chloransulam | soybean | 0.3 oz | 11 |
| prosulfuron | corn | 0.036 lb | 81 |

TABLE 2

Effect of glyphosate and trifloxysulfuron on kudzu

| Treatment | Rate glyphosate (lb./A) trifloxysulfuron (g/A) | Kudzu Control (%) |
|---|---|---|
| trifloxysulfuron | 4.25 | 72 |
| glyphosate | 0.35 | 33 |
| trifloxysulfuron glyphosate | 4.25 + 0.35 | 83 |
| glyphosate | 0.7 | 95 |
| trifloxysulfuron glyphosate | 4.25 + 0.7 | 93 |
| glyphosate | 1 | 97 |
| trifloxysulfuron glyphosate | 4.25 + 1 | 97 |
| Lsd | | 10 |

TABLE 3

Effect of herbicide mixtures on kudzu regrowth at 6 WAT.

| | Kudzu Regrowth Gram dry wgt per plot |
|---|---|
| Glyphosate | .52 |
| Atrazine | .59 |
| Glyphosate + atrazine | .72 |
| Metribuzin | .51 |
| Glyphosate + metribuzin | .51 |
| Glyphosate + trifloxysulfuron | .09 |
| Control | .81 |
| Lsd | .41 |

TABLE 4

Treatment combinations for FIG. 4.
Summary of Treatments for FIG. 4

| Treatment | Composition | Rate (units/A) |
|---|---|---|
| 1 | Glyphosate | 22 fl oz |
| 2 | Trifloxysulfuron | 0.15 oz |
| 3 | Glyphosate + trifloxysulfuron | 22 fl oz + 0.15 oz |
| 4 | Glyphosate + trifloxysulfuron | 11 fl oz + 0.15 oz |
| 5 | Flumetsulam | 1.33 oz |
| 6 | Glyphosate + flumetsulam | 22 fl oz + 1.33 oz |
| 7 | Glyphosate + flumetsulam | 11 fl oz + 1.33 oz |
| 8 | Pyrithiobac | 1.8 oz |
| 9 | Glyphosate + pyrithiobac | 22 fl oz + 1.8 oz |
| 10 | Glyphosate + pyrithiobac | 11 fl oz + 1.8 oz |

TABLE 5

Herbicide cost for kudzu control.
Comparative Herbicide Mixtures for Kudzu Control

| Herbicide | Recommend Rates (units/A) | Cost, $/unit |
|---|---|---|
| Glyphosate | 80-106 fl oz (22 fl oz*) | 0.28/fl oz |
| Trifloxysulfuron | not listed for kudzu (0.15 oz*) | 75/oz |
| Flumetsulam | not listed for kudzu (1.33 oz*) | 10-12/oz |
| Pyrithiobac | not listed for kudzu (1.8 oz*) | 19/oz |
| Metsulfuron Methyl | 4 oz | 20-27/oz |
| Picloram | 1-2 lb | 48/lb |
| Triclopyr | 6-9 lb | 20-33/lb |
| Clopyralid | 0.5 lb | 105/lb |

*Recommended Rates per this invention

We claim:

1. A method for killing weeds, said method comprising applying to said weeds a herbicidally effective amount of a herbicidal composition comprising glyphosate and trifluxosulfuron; wherein said weeds are kudzu.

2. The method of claim 1, wherein said herbicidal composition is applied to weeds in Autumn.

3. The method of claim 1, wherein said herbicidal composition is applied to weeds in Spring.

4. The method of claim 1, wherein said method comprises applying about 1 to about 2 lb of glyphosate per acre plus about 0.15 to about 0.30 oz. per acre trifluxosulfuron.

\* \* \* \* \*